United States Patent
Allsworth (10) Patent No.: US 11,617,521 B2
(45) Date of Patent: Apr. 4, 2023

(54) MULTIPLE BREATH SAMPLING METHOD

(71) Applicant: OWLSTONE MEDICAL LIMITED

(72) Inventor: Max Allsworth, Cambridge (GB)

(73) Assignee: OWLSTONE MEDICAL LIMITED, Cambridge (GB)

(*) Notice: Subject to any disclaimer, the term of this patent is extended or adjusted under 35 U.S.C. 154(b) by 655 days.

(21) Appl. No.: 16/609,287

(22) PCT Filed: May 17, 2018

(86) PCT No.: PCT/GB2018/051337
§ 371 (c)(1),
(2) Date: Oct. 29, 2019

(87) PCT Pub. No.: WO2018/211280
PCT Pub. Date: Nov. 22, 2018

(65) Prior Publication Data
US 2021/0212597 A1    Jul. 15, 2021

(30) Foreign Application Priority Data
May 18, 2017 (GB) .................................... 1707999

(51) Int. Cl.
| | | |
|---|---|---|
| *B01D 53/02* | (2006.01) | |
| *A61B 5/097* | (2006.01) | |
| *A61B 5/08* | (2006.01) | |
| *B01J 20/20* | (2006.01) | |
| *B01J 20/26* | (2006.01) | |
| *B01J 20/28* | (2006.01) | |

(52) U.S. Cl.
CPC .............. *A61B 5/097* (2013.01); *A61B 5/082* (2013.01); *B01J 20/20* (2013.01); *B01J 20/262* (2013.01); *B01J 20/28052* (2013.01)

(58) Field of Classification Search
CPC .......... A61B 5/082; A61B 5/097; B01J 20/20; B01J 20/262; B01J 20/28052
See application file for complete search history.

(56) References Cited

U.S. PATENT DOCUMENTS

| 6,248,078 B1 * | 6/2001 | Risby ..................... A61B 5/097 |
| | | 73/23.3 |
| 2003/0109794 A1 * | 6/2003 | Phillips ................ G01N 1/2214 |
| | | 977/905 |

(Continued)

FOREIGN PATENT DOCUMENTS

| WO | WO 2017/187120 | 11/2017 |
| WO | WO 2017/187141 | 11/2017 |

OTHER PUBLICATIONS

Search Report & Written Opinion issued in App. No. PCT/GB2018/051337 (dated 2018).

*Primary Examiner* — Christopher P Jones
(74) *Attorney, Agent, or Firm* — Barnes & Thornburg LLP (57) ABSTRACT

Disclosed is a method for collecting different selected exhaled breath samples, or fractions thereof, on a single sample capture device, the method comprising the steps of: (a) collecting a first exhaled breath sample by contacting the sample with a capture device comprising an adsorbent material; (b) collecting a second exhaled breath sample by contacting the second sample with said capture device, wherein the first and second exhaled breath samples are caused to be captured on the capture device in a spatially separated manner.

18 Claims, 4 Drawing Sheets

(56) References Cited

U.S. PATENT DOCUMENTS

| | | | |
|---|---|---|---|
| 2003/0139681 A1* | 7/2003 | Melker | A61B 5/0836 600/532 |
| 2005/0177056 A1 | 8/2005 | Giron et al. | |
| 2011/0077545 A1* | 3/2011 | Eichler | A61B 5/145 600/538 |
| 2014/0228699 A1 | 8/2014 | Causevic et al. | |
| 2015/0335267 A1 | 11/2015 | Cormier et al. | |
| 2017/0303822 A1* | 10/2017 | Allsworth | A61B 5/097 |
| 2017/0303823 A1* | 10/2017 | Allsworth | A61B 10/00 |

* cited by examiner

MULTIPLE BREATH SAMPLING METHOD

CROSS REFERENCE TO RELATED APPLICATIONS

This application is a U.S. nationalization under 35 U.S.C. § 371 of International Application No. PCT/GB2018/051337, filed May 17, 2018, which claims priority to United Kingdom Patent Application No. 1707999.7, filed May 18, 2017. The disclosures set forth in the referenced applications are incorporated herein by reference in their entireties.

FIELD OF THE INVENTION

The present invention relates to a method of obtaining a multiple samples of breath from a subject, using a breath sampling device.

BACKGROUND OF THE INVENTION

The metabolome is the aggregate of small molecules that originate from metabolic processes throughout the body. Metabolomic analysis is appealing for biomedical applications as relatively small changes in gene-expression or protein activity can have a profound effect on the concentrations of downstream metabolites. A significant fraction of these metabolites are volatile. These biomarkers are of specific interest in health and disease as they are excreted through breath, urine, faeces and skin providing non-invasive access. Volatile biomarkers (VBs) consist of both volatile organic compounds (VOCs) and Volatile inorganic compounds (VICs). Examples of VBs implicated in health and disease include alkanes, alkenes, acetone, isoprene, NO, CO and aldehydes.

Any change in the function of an organism changes cellular metabolism by definition. Consequently this affects the metabolome and its volatile fraction. The resulting changes in VBs may therefore serve as biomarkers for assessment of a wide range of normal physiological and pathophysiological processes.

In view of the foregoing, there is interest in obtaining samples of breath from a subject for analysis for detection of one or more biomarkers or other analytes. Apparatus for facilitating the capture of a breath sample from a patient is known, and particular examples include those described in U.S. provisional patent application 62/327,200 and WO2017/187120.

The device disclosed in WO2017/187120 comprises a mask portion which, in use, is positioned over a subject's mouth and nose, so as to capture breath exhaled from the subject. The exhaled breath samples are fed into tubes containing a sorbent material, to which the compounds of interest adsorb. After sufficient sample has been obtained, the sorbent tubes are removed from the sampling device and the adsorbed compounds desorbed (typically by heating) and subjected to analysis to identify the presence and/or amount of any particular compounds or other substances of interest. The preferred analytic technique is field asymmetric ion mobility spectroscopy (abbreviated as "FAIMS").

A refinement of the method described in WO2017/187120 is disclosed in WO2017/187141. In that document, it is taught to use breath sampling apparatus substantially of the sort described in WO2017/187120, but in a way such as to selectively sample desired portions of a subject's exhaled breath, the rationale being that certain biomarkers or other analytes of interest being relatively enriched in one or more fractions of the exhaled breath, which fractions themselves are relatively enriched in air exhaled from different parts of the subject's body (e.g. nostrils, pharynx, trachea, bronchioles, alveoli etc.). In a simple embodiment, the method allows for selective sampling of exhaled breath fractions representing respectively the subject's upper or lower respiratory tract.

US 2014/0228699 (Causevic et al) discloses a "sampling and storage registry device for breath gas analysis". In one embodiment, the device may be used to "capture" multiple samples of breath in a single sample tube. The prior art document also discloses that, if desired, the different breath samples can be separated from adjacent samples in the sample tube by introduction of intervening portions of inert gas (such as nitrogen) or ambient air.

The document does not disclose how the plurality of samples are "captured" in the tube, nor does it describe in detail how the "captured" samples are released from the sample tube for analysis.

The present invention aims to provide a method which, at least in some respects, provides further improvements over the foregoing.

SUMMARY OF THE INVENTION

In a first aspect, the invention provides a method for collecting different selected exhaled breath samples, or fractions thereof, on a single breath sample capture device, the method comprising the steps of:
 (a) collecting a first exhaled breath sample by contacting the sample with a capture device comprising an adsorbent material;
 (b) collecting a second exhaled breath sample by contacting the second sample with said capture device, wherein the first and second exhaled breath samples are caused to be captured on the capture device in a spatially separated manner.

In preferred embodiments the capture device comprises an adsorbent material in the form of a porous polymeric resin. Suitable adsorbent materials include Tenax® resins and Carbograph® materials. Tenax® is a porous polymeric resin based on a 2,6-diphenyl-p-propylene oxide monomer. Carbograph® materials are graphitized carbon blacks. Especially preferred is Tenax GR, which comprises a mixture of Tenax® TA and 30% graphite. A particular preferred Carbograph® adsorbent is Carbograph 5TD. In one preferred embodiment the capture device comprises both Tenax GR and Carbograph 5TD.

The capture device is conveniently a sorbent tube. These are hollow metal cylinders, typically of standard dimensions (3½ inches in length with a ¼ inch internal diameter) packed with a suitable adsorbent material.

There are many ways of achieving the necessary spatial separation between the first and second samples on the capture device, and the preferred method may depend on several factors including, for example, the volume of the samples, the nature and size of the capture device, and the identity of any particular analytes of interest.

In one simple embodiment, the capture device is caused to move relative to a breath sampling conduit, during a time interval between the end of the collecting of the first exhaled breath sample and the start of the collecting of the second exhaled breath sample. In this way, the first and second breath samples may be collected on spatially separated, preferably distinct, portions of the collecting device. The breath sampling conduit may be any pipe, tube, cylinder, hose or the like by which exhaled breath from a subject is fed into contact with the capture device.

The capture device may be moved relative to the breath sampling conduit in any suitable motion e.g. rotational, translational, or a combination thereof. The capture device may be static and the breath sampling conduit may move, or vice versa. Alternatively both the breath sampling conduit and the capture device may move.

In another simple, and preferred, embodiment a spatial separation is achieved between the first and second breath samples by causing the first collected sample to move or migrate along and/or within the capture device, prior to contacting the second sample with the capture device. This can be achieved, for example, by causing a flow of gas through the capture device, which can be enough to cause the sample to migrate, since it is bound only weakly to the sorbent material. The person skilled in the art can, with the benefit of the present disclosure, readily select an appropriate sorbent material for which the analyte or analytes of interest have relatively low affinity.

A measure of the affinity of an analyte for a sorbent material is the "breakthrough volume", which is usually determined experimentally rather than theoretically (see, for instance, http://www.sisweb.com/index/referenc/tenaxta.htm). The breakthrough volume is usually expressed in terms of litres per gram of sorbent material, which is the volume of gas required to elute the organic compound off 1.0 gram of resin at a particular temperature. The elution is generally performed using an inert and/or irrelevant gas (e.g. nitrogen).

More especially, there is preferably a time interval between the end of the period in which the first exhaled breath sample is collected, and the start of the period in which the second exhaled breath period is collected. During this time interval the first captured sample migrates or moves along the capture device, such that there is a clear spatial separation between the first and second samples on the capture device. Conveniently, during this time interval the capture device may be contacted with an irrelevant gas feed, such as pure nitrogen or helium, or a clean (i.e. activated carbon filtered) air supply, which irrelevant gas feed will not contain detectable quantities of any analytes of interest.

A suitable duration for the intervening time period can be estimated by the person skilled in the art based on the rate of movement of the breath samples along the capture device and the size of the spatial separation desired between the samples. The duration of the intervening time period will typically be at least 30 seconds, preferably at least 45 seconds, and more preferably at least 60 seconds. Most preferably the time interval will be in the range 1.0 to 5.0 minutes. Conversely, the duration of the collection of individual breath samples will typically be about 30 seconds to 1 minute per breath sample.

In embodiments of this type, in which an exhaled breath sample migrates or otherwise moves along the capture device over time, both the first and second exhaled breath samples may be contacted with the same initial contact region of the capture device, but with a temporal separation which, in turn, (because of the movement of the breath sample along the capture device) creates a spatial separation between the captured breath samples.

It will be apparent to the person skilled in the art that the method of the invention can be adapted so as to allow the capture of a third or further exhaled breath samples. For example, by causing further movement of the capture device relative to a breath sampling conduit; or by allowing further intervening time periods between successive periods of breath sampling, so as to allow previously collected breath samples to move or migrate along the capture device. The number of different samples which can be captured on a single capture device will depend on the size of the captured samples, the volume or capacity of the capture device, and the amount of spatial separation required between captured samples. If desired, two or more capture devices may be operably coupled, so as to extend the effective length of the capture device. However, even collecting just two samples of breath on a single capture device effectively doubles the capacity of the device, or allows the size of the sampling apparatus to be substantially reduced.

The first and second exhaled breath samples (and subsequent samples, if present) may be collected from different subjects. Alternatively, and more typically, the first and second breath samples may be collected from the same subject. In this latter instance, the first and second samples might represent different selected fractions of the subject's exhaled breath (e.g. relatively enriched with air from the subject's upper and lower respiratory tract respectively). Alternatively, between the first and second sampling, the subject may be treated with a substance which causes a distinctive change in their exhaled breath which facilitates a medical diagnosis or prognosis, for example.

There are two distinct situations or applications in which the method of the present invention may be especially useful. The first is in the situation where it is desired to investigate or analyse the presence and/or concentration of two or more different analytes in breath samples from a subject: temporarily capturing two different samples on the same adsorbent capture device facilitates the sampling process so that, for example, it is not necessary to halt the sampling to permit the replacement of the capture device with a fresh capture device to capture the second sample.

The second situation is where is it desired to investigate or analyse the kinetics of an analyte in a breath sample: using the method of the invention allows a first breath sample to be collected during a first time period, and a second breath sample to be collected during a second (later) time period, both breath samples being temporarily captured on the same adsorbent capture device. A particular example of this situation is a "wash-out" type experiment, which is used to analyse the kinetics of the presence of an analyte in breath samples over time. In a typical such experiment, a substance is administered to a human subject. The substance is typically a GRAS ("Generally Recognised as Safe") substance. The substance may be administered orally, intranasally or by injection (e.g. intravenously or subcutaneously) or any other suitable route, but a non-invasive route such as oral administration is generally preferred. The substance may be a single compound, or a mixture. Preferably the substance is such that, after administration to the subject, the substance per se or a component thereof is readily detectable in the exhaled breath of the subject or, in the alternative, a metabolite or other derivative of the substance is produced in vivo in the subject's body and this metabolite or other derivative is readily detectable in the exhaled breath from the subject.

The concentration or amount of the substance, and/or its metabolite or other derivative, may be determined in absolute or relative terms in the first breath sample (collected at a first time period) and in the second breath sample (collected at a later, second time period), thus permitting analysis of the kinetics or rate of change of concentration thereof over time. In the method of the invention, both first and second breath samples (and optionally third and further breath samples) are collected on the same adsorbent capture device and then typically separately desorbed therefrom for analysis.

Where short term (e.g. over a period of 6 hours or less, typically over a period of 1 hour or less) changes in breath VOCs are investigated, it is desirable to investigate the rate of change of the VOC concentration, and determining this parameter accurately and in a reproducible and robust manner requires multiple measurements in a short period of time. In such situations, the present invention permits the collection of such multiple breath samples using fewer capture devices. This is a significant saving in cost and time, but also provides improved data integrity, as the capture device can be left in place without the interruptions of capture tube replacement or mask removal. Specific examples of this sort include:

a) Exposure to an exogenous VOC such as benzene in a place of work, a petrol station or a high traffic area and monitoring the level drop in breath (as a proxy for blood) after exposure; and b) Monitoring a biological breath compound such as acetone or isoprene as a function of exercise while simultaneously measuring heart rate, allowing a personalised exercise routine to be developed based on a particular subject's transition to fat burning exercise.

Preferably, the spatial separation of the first and second breath samples on the capture device permits the samples to be individually desorbed from the capture device and/or individually analysed. For example, the spatial separation can be used to cause a temporal separation of the desorption of the samples from the capture device. In a preferred arrangement, the two different samples will be subjected to thermal desorption at the same (i.e. +/— 0.5° C.) temperature but, because of their spatial separation, will exit from the capture device at different times.

For example, the desorption temperature can be selected to be a temperature that is between the boiling points of two different analytes of interest. Alternatively, and less preferably, a lower boiling point analyte is desorbed at one temperature, and then the temperature is increased to above that of a second analyte's boiling point. The advantage of using a single (lower) temperature to desorb both analytes is reduced complexity of the desorption method, and also reduced risk of higher temperature degrading the analyte.

The samples, once desorbed from the capture device, may be passed directly into an analytic instrument for analysis, or may be further temporarily stored on a further temporary storage device. In one embodiment, for example, the two or more samples are desorbed separately from the capture device and all are immediately passed into an analytic instrument. Alternatively, the two or more samples are separately desorbed from the capture device and all stored, separately, on respective further storage devices (e.g. sorbent tubes) for subsequent analysis. Yet another possibility is for at least one of the samples to be desorbed from the capture device and analysed substantially immediately, whilst at least one of the samples is desorbed from the capture device for storage on a further storage device for subsequent analysis.

The samples, once desorbed from the capture device, may be subjected to some form of processing prior to analysis. This might include, for example, one or more of the following: pooling of multiple samples; concentration; fractionation; purification.

The analytic method/apparatus used to analyse the samples may be any suitable method compatible with the samples and the analytes(s) of interest. Suitable analytical methods/apparatus may include FAIMS, gas chromatography and GC-MS.

Options for analysis include:

(i) A staged desorption where the tube is reverse desorbed at a similar or raised temperature relative to the sample collection temperature so that the last breath collection elutes first; the inert gas which is used to desorb the sample passes through a focusing cold trap which collects the VOCs before the cold trap is fired (rapidly heated) onto a GC column and the target compound is quantitated with a mass spectrometer. This is repeated several times until the tube has been flushed of all the individual collections of the tube.

(ii) It is not necessary to wait for the GC column to elute all compounds, as compounds of interest will always be temporally separated, so the desorption and firing of the cold trap can be done in quick succession so the overall measurement time can be reduced. This results in a single chromatogram with the same compound appearing several times (though there are many interfering peaks as these will also be repeated).

(iii) For some target compounds the GC could be removed entirely and the tube desorption could be fed into a mass spectrometer in real-time.

The invention will now be described way of illustrative example and with reference to the accompanying drawings, in which.

DETAILED DESCRIPTION OF EMBODIMENTS

Example 1

Figure 1:
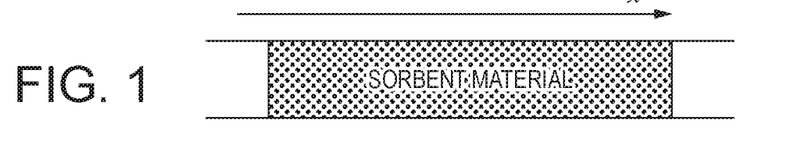
FIG. 1 is a cross-sectional view through one embodiment of a typical capture device of use in performing the method of the invention.

Referring to FIG. 1, a typical capture device comprises a metallic tube 2 substantially filled with a sorbent material 4 (in this instance a mixture of Tenax® GR and Carbograph® 5TD). This material is such that exhaled breath samples will tend to move along the capture device, in the direction x indicated by arrow 6. The capture device is for use with sampling apparatus as disclosed in WO2017/187120.

Figure 2:
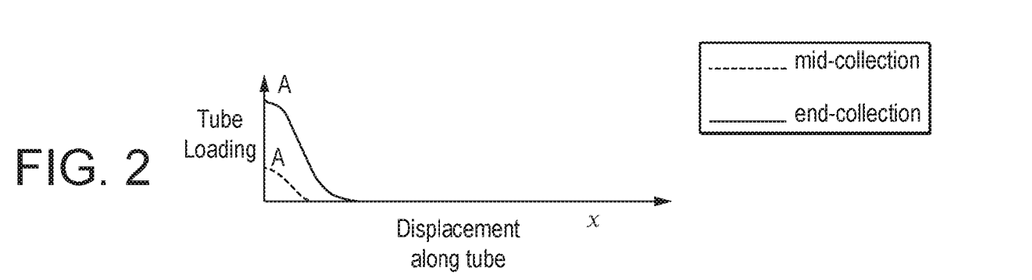
FIGS. 2-4 are representative graphs illustrating the migration of first and second exhaled breath samples over time along the capture device illustrated in FIG. 1.

As seen in FIG. 2, a first breath sample, comprising analyte A is contacted, via a breath sampling conduit, with one end of the capture device. The amount of analyte A, and approximate position thereof collected on the capture device during an early part of the first sampling period is indicated by the broken line. The amount of analyte A and approximate position thereof on the capture device near the end of the first sampling period is indicated by the solid line.

Figure 3:
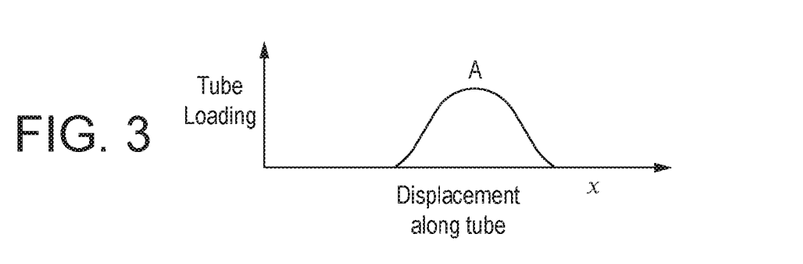

As seen in FIG. 3, breath sampling is discontinued and, instead of exhaled breath, a filtered clean air supply is fed into the sampling conduit and contacted with the capture device. During this time interval, the first breath sample migrates along the capture device.

Figure 4:
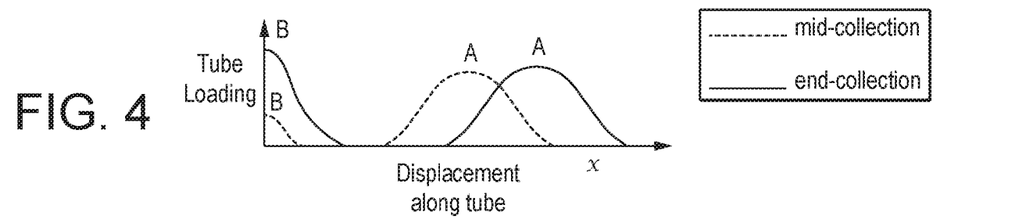

In FIG. 4, after a suitable length of time has elapsed, the collection of the second sample of exhaled breath is commenced, as shown by the appearance of analyte B in the capture device, which analyte is present in the second breath sample. The amount and position of analytes A and B during an early part of the second breath sampling period is indicated by the broken lines, and the amount and approximate positions of analytes A and B near the end of the second sampling period is indicated by the solid lines. As is apparent from the figure, during the sampling period, both samples migrate downstream along the capture device, but due to the intervening time period between the first and second sampling periods, the samples are spatially separated on the capture device. In this hypothetical example, both analytes A and B have substantially the same rate of movement along the capture device. The length of the intervening time period between sampling periods can be increased if, for instance, the rate of movement of analyte B on the capture device is greater than that of analyte A. Conversely the intervening time period can be shortened if the rate of movement of analyte A along the capture device is greater than that of analyte B.

It will also be apparent that a third breath sampling period may be added, following a further intervening time period (in which a clean air supply is provided to the sampling conduit). In order to retain the first breath sample on the capture device, whilst capturing a third breath sample, it may be necessary to use a longer capture device. This could be achieved by, for example, connecting two sorbent tubes in tandem, end-on-end.

Figure 5:
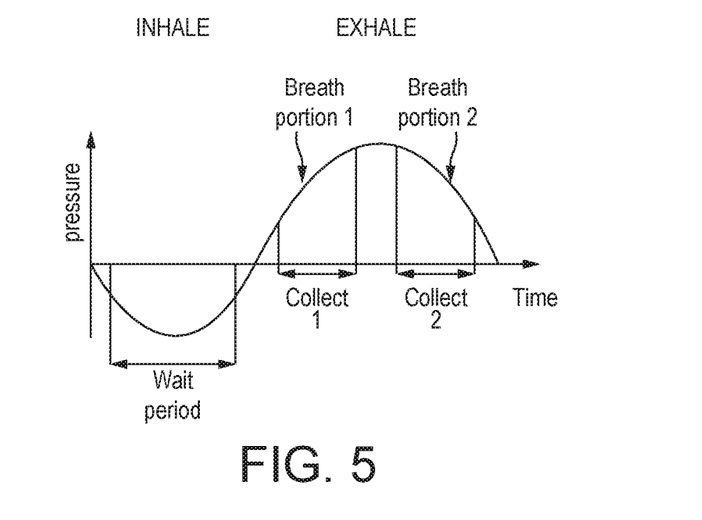
FIG. 5 is a representative graph illustrating pressure changes in breath sampling apparatus as a subject inhales and exhales (and how these can be used to select desired breath fractions for collection)

FIG. 5 is a graph of pressure against time during one breath cycle, the pressure being the pressure inside a mask portion of breath sampling apparatus of the sort disclosed in WO2017/187120. As can be observed in the Figure, when the subject inhales, the pressure inside the mask falls, and increases when the subject exhales.

The first breath sample is obtained by collecting breath exhaled from the subject during the early part of the exhalation (denoted "COLLECT 1"). This portion of exhaled breath is repeatedly sampled during the first breath sampling period over a plurality of breath cycles (typically at least 100 cycles), so as to collect sufficient sample to detect analyte A.

During the second breath sampling period, breath sample is obtained during the later part of the exhalation (denoted "COLLECT 2"). Again, this portion of exhaled breath is repeatedly sampled during the second breath sampling period over a plurality of breath cycles (typically at least 100 cycles), so as to collect sufficient sample to detect analyte B.

Figure 6:
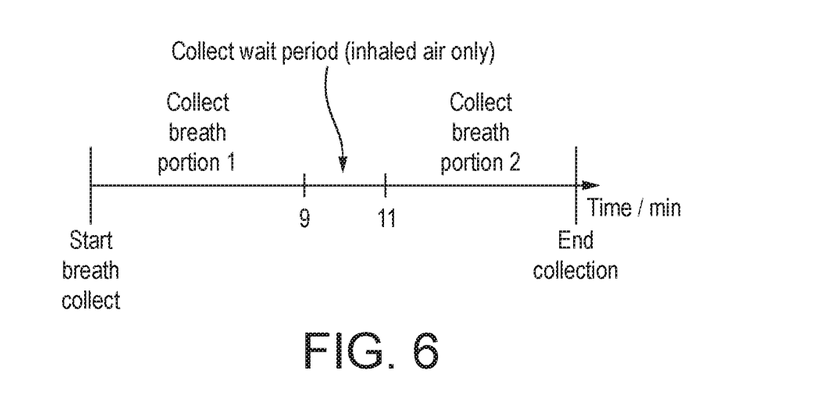
FIG. 6 is a representative time line showing collection of first and second exhaled breath samples.

FIG. 6 is a schematic illustration showing the timeline (in minutes) for the first and second breath sampling periods. The first breath sampling period commences at t=0, and continues for about 9 minutes. Sampling is then discontinued for 2 minutes (the "intervening time period"). During this time, the capture device is fed only inhaled air via the sampling conduit—this is a clean air supply which is provided to the subject.

After the 2 minute intervening period has elapsed, the second breath sampling period is commenced, and this continues for about 9 minutes, so that the total length of time take to complete the process is about 20 minutes (i.e. two sampling periods each of about 9 minutes, with a 2 minute intervening period).

Figure 7:
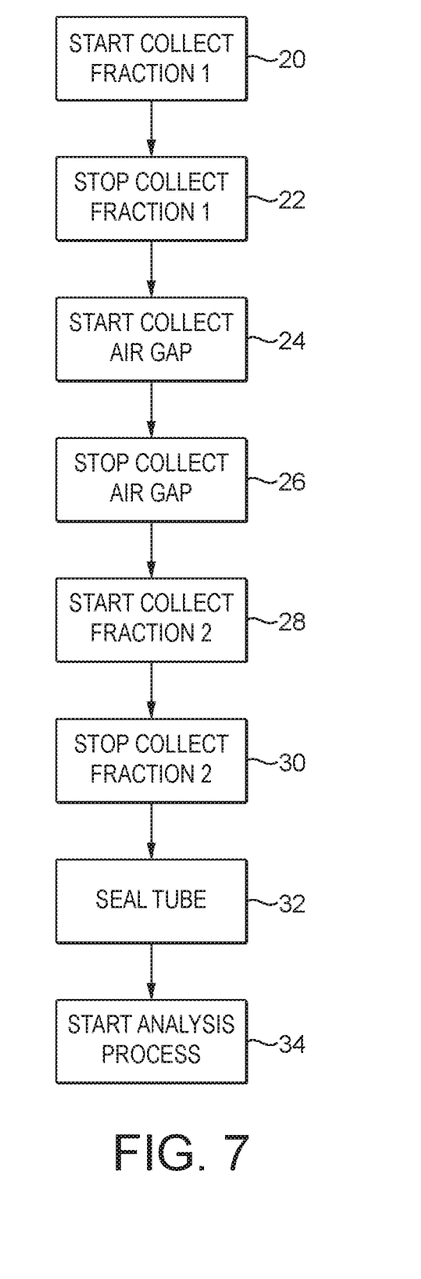
FIG. 7 is a sample flow chart describing one embodiment of a method in accordance with the invention.

A particular illustrative embodiment of the method of the invention is now described, with reference to FIG. 7. FIG. 7 is a flow chart illustrating the performance of a method in accordance with the invention, using breath sampling apparatus substantially as disclosed in WO2017/187120.

In box 20, the first breath sampling period is commenced. A sampling pump is configured to pass exhaled breath from a subject (during a specified range of pressure sensor values) so as to collect a fraction of breath relatively enriched for air from the subject's lower respiratory tract. In this instance the analyte of interest is butanone. The flow rate of exhaled air is measured, and the first breath sampling period is terminated after 500 mls of sample has been collected (box 22).

In box 24 the intervening time period (i.e. the time between first and second breath sampling periods) is commenced. The apparatus is arranged so that only inhaled air is passed to the capture tube. In box 26 the intervening period is terminated, once enough air has been collected to allow each of the first and second breath samples to remain spatially separated on the capture device. This may be, for example, two times the volume of the first sample.

In box 28 the second breath sampling period is commenced. The sampling is performed in essentially the same way as in the first sampling period, except that in the second breath sampling period, exhaled breath is selectively captured during an early part of exhalation, so as to obtain a sample which is relatively enriched with air from the subject's upper respiratory tract. In this sample, the analyte of interest is hexanal. Sampling is terminated (box 30) after 500 mls of sample has been collected—again this is calculated by measurement of the flow rate of exhaled air.

Substantially immediately after sampling, the capture device is sealed (box 32) and may then be subjected to analysis (box 34). To analyse the samples captured on the capture device, the samples must be desorbed. A cap is placed on the end of each sorbent tube. These caps have only a small hole through them that helps minimise inward diffusion of ambient air into the tubes. The tubes are then placed in a thermal desorber (e.g. a Markes TD-100xr). Each tube is then automatically fed into the region of the thermal desorber (TD) apparatus where desorption will take place. This region has two ports that mate with the tube. The outlet port is heated to prevent condensation. The tube is oriented so that gas flow is in the opposite direction to that occurring during sample collection. A heated U-shaped member comes into contact along the full length of the tube, to raise its temperature to the desired level and gas flow is commenced. The following protocol is used: place tube in a thermal desorber (TD), with helium flowing through the TD at a constant rate of 50 mL/min; desorb sample 1 by raising the temperature to 50° C.; the output of tube is collected on a cold trap, to remove any water, the output of the cold trap is then passed to GC-FAIMS or GC-MS spectrometer for analysis; Desorb sample 2 by raising the temperature to 300° C.; the output of tube is collected on a cold trap, to remove any water, and the output of the cold trap passed to GC-FAIMS or GC-MS spectrometer for analysis.

Example 2

Measuring VOC biomarkers over time offers a completely non-invasive way of monitoring health, diagnosing disease and assessing response to therapy. This example describes how the Applicant's "Breath Biopsy" platform, as outlined in WO2017/187120, can be used to capture multiple breath samples over time, uncovering detailed changes in the concentration of VOCs present in breath.

Single measurements of any biomarker provide only a snapshot of an individual's current state. While this provides useful information, point measurements do not give information about the baseline abundance of biomarkers for that individual. Making multiple measurements over time allows detection of changes in biomarker concentration that can indicate deviation from a baseline state and may point to the onset of disease or a successful response to therapy.

"Breath Biopsy", can be used to monitor longitudinal changes in exhaled VOCs, and discover biomarkers for monitoring, for example, disease burden, disease recurrence or patent response to therapy.

Successful longitudinal measurements require highly reproducible sampling and analysis techniques.

By measuring VOCs in breath following ingestion of a peppermint capsule we show that "Breath Biopsy" can be used to observe the decrease in target compounds over time using repeated, robust breath collection and analysis over a period of 8 hours.

Breath Biopsy Workflow

After ingestion of the peppermint capsule, breath samples are collected from an individual onto a Breath Biopsy Cartridge every 30 minutes for 8 hours using a ReCIVA Breath Sampler and CASPER Air Supply (as described in WO2017/187120). Using the method of the invention, several such samples can be captured on a single sorbent tube, thereby greatly reducing the number of capture devices required to perform such extended sampling. For comparison, two breath collections were made from the same individual prior to ingestion to provide a baseline concentration for the VOCs of interest. Breath samples were analysed in the Breath Biopsy Clinical Lab by FAIMS and mass spectrometry.

VOCs in Breath Following Capsule Ingestion

Figure 8:
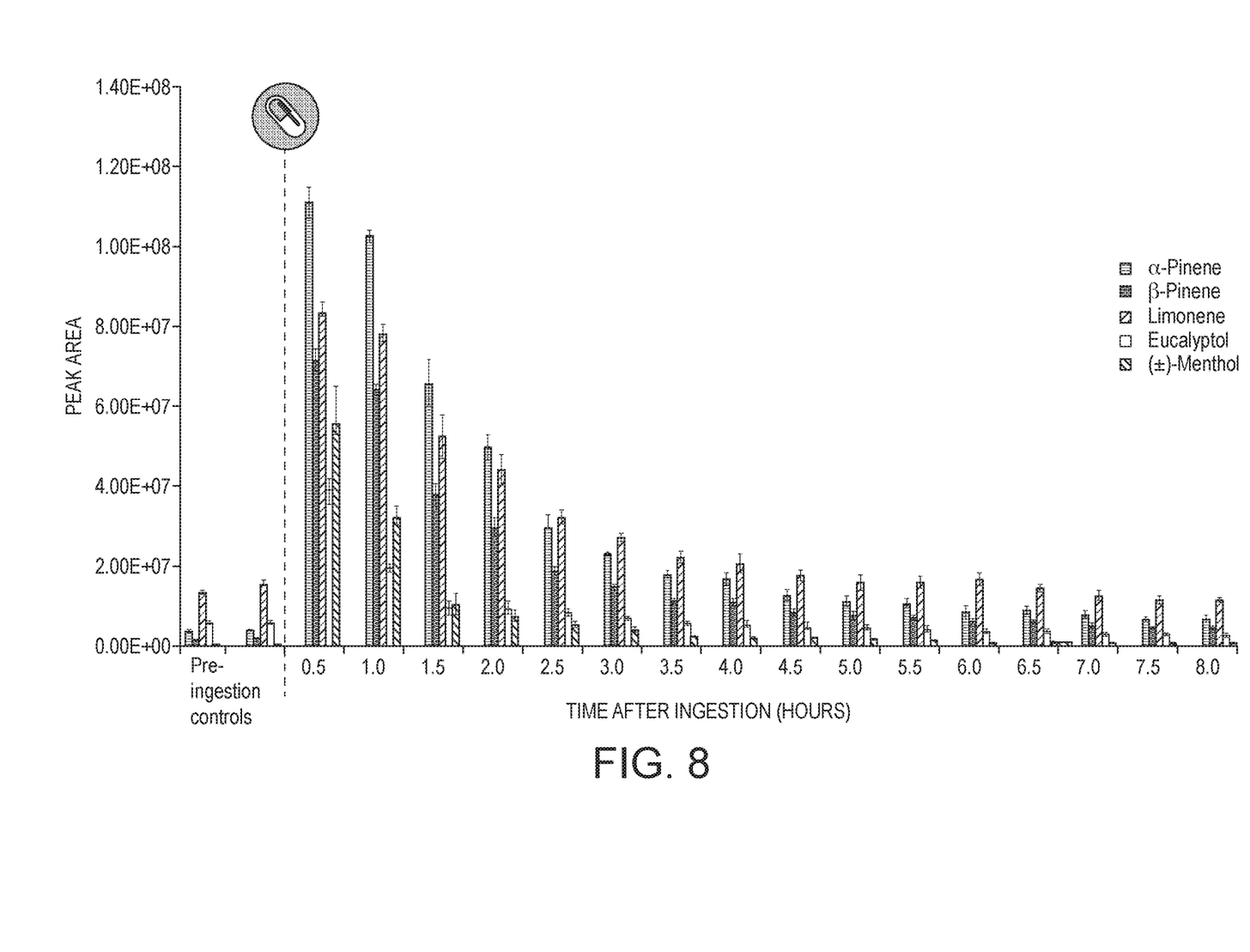
FIG. 8 is a graph of peak area against time, showing the results for a "wash out" experiment using a peppermint capsule.

Analysis of breath captured 30 minutes after consumption of the peppermint capsule shows a large increase in the VOCs α-pinene, β-pinene, limonene, eucalyptol and (±)-menthol compared to baseline pre-ingestion controls captured immediately prior to taking the capsule (FIG. 8). FIG. 8 shows the peppermint-related VOCs in sampled breath before, and at 30 minute intervals after, consumption of a peppermint capsule by a normal human subject. Breath samples were collected using the ReCIVA apparatus as described elsewhere and analysed using TD-GC-TOF mass spectrometry. For each time point, the VOCs detected were (from left to right) (i) α-pinene, (ii) β-pinene, (iii) limonene, (iv) encalyptol and (v) menthol. The first two time points are the results for the pre-ingestion controls. The dotted line and capsule symbol indicate time zero when the capsule was ingested. The arbitrary units on the Y axis are the peak area, while the x axis shows time after ingestion, in hours. The most abundant of these peppermint-related compounds are α-pinene, β-pinene and limonene. Limonene is present at part-per-trillion (ppt) concentrations.

Breath collections made every 30 minutes after this initial capture show a consistent decrease in the target VOCs over time. Captures made from 6.5 hours after consumption show the levels of the target VOCs decreasing to baseline levels. All of the target compounds display a similar washout curve over time.

In this study, standard deviations are calculated for the 4 replicate samples collected on the breath Biopsy Cartridge at each breath collection (Table 1). This gives an indication of the high intra-sample reproducibility of breath sampling and analysis using the Breath Biopsy platform.

TABLE 1

Mean average and range of % relative standard deviation (% RSD) of peak area for compounds shown in FIG. 8.

| % RSD | α-pinene | β-pinene | limonene | eucalyptol | (±)-menthol |
|---|---|---|---|---|---|
| average | 8.05 | 7.99 | 7.38 | 11.26 | 27.53 |
| min | 1.34 | 1.99 | 2.51 | 4.94 | 4.14 |
| max | 18.60 | 13.02 | 11.60 | 19.46 | 61.83 |

Note
high max % RSDs are for points close to baseline where VOC concentrations were much lower.

Summary

This study demonstrates that the Breath Biopsy platform can be used to reproducibly capture and analyse breath samples during a longitudinal study. Using a peppermint capsule as a surrogate pharmaceutical, the levels of peppermint-related compounds in breath were found to increase rapidly after ingestion, and subsequently decrease following a washout curve over time.

The invention claimed is:

1. A method for collecting different selected exhaled breath samples, or fractions thereof, on a single sorbent tube capture device, the method comprising the steps of:
    (a) collecting a first exhaled breath sample by contacting the sample with said sorbent tube capture device;
    (b) collecting a second exhaled breath sample by contacting the second sample with said sorbent tube capture device, wherein the first and second exhaled breath samples are caused to be captured on the sorbent tube capture device in a spatially separated manner.

2. The method according to claim 1, wherein the sorbent tube capture device comprises a porous polymeric sorbent resin.

3. The method according to claim 1, wherein the sorbent tube capture device comprises, as a sorbent material, a polymer of 2,6-diphenyl-p-phenylene oxide; and/or graphite.

4. The method according to claim 1, wherein the first and second breath samples are captured on the sorbent tube capture device in a spatially separated manner by causing the first collected sample to move or migrate along the capture device, prior to contacting the second sample with said sorbent tube capture device.

5. The method according to claim 1, wherein there is an intervening time period of at least 30 seconds between the end of the first sample collection and the start of the second sample collection.

6. The method according to claim 1 wherein, between the end of the first sample collection and the start of the second sample collection, the sorbent tube capture device is contacted with a clean feed of an inert gas.

7. The method according to claim 1, further comprising contacting the sorbent tube capture device with a third exhaled breath sample.

8. The method according to claim 7, wherein there is an intervening time period of at least 30 seconds between the end of the second sample collection and the start of the third sample collection.

9. The method according to claim 1, wherein the first and second exhaled breath samples are obtained from different subjects.

10. The method according to claim 1, wherein the first and second exhaled breath samples are obtained from different parts of a breathing cycle from the same subject.

11. The method according to claim 1, further comprising the step of desorbing the first and second breath samples from the sorbent tube capture device.

12. The method according to claim 11, wherein the first and second breath samples are desorbed separately from the sorbent tube capture device.

13. The method according to claim 12, wherein the first and second breath samples are desorbed from the sorbent tube capture device at the same temperature.

14. The method according to claim 11, further comprising the step of chemical analysis of the samples.

15. The method according to claim 14, wherein the chemical analysis comprises detecting the presence and/or measuring the concentration of at least one analyte.

16. The method according to claim 1, which further comprises, prior to collecting the first and second exhaled breath samples, the step of administering a substance to a subject, which substance, or a metabolite or other derivative thereof formed in the subject, is detectable in a breath sample obtained from the subject.

17. The method according to claim 16, wherein the substance administered to the subject is a GRAS substance.

18. The method according to claim 16, wherein the concentration or amount of the administered substance or metabolite or other derivative thereof is determined in absolute or relative terms in the first breath sample collected at a first known time point and in the second breath sample collected at a second known time point, thereby permitting analysis of the change in concentration or amount of the administered substances or metabolite or other derivative thereof in the exhaled breath of the subject over time.

* * * * *